(12) United States Patent
Spurr

(10) Patent No.: US 7,087,761 B2
(45) Date of Patent: Aug. 8, 2006

(54) CYCLIZATION PROCESS FOR SUBSTITUTED BENZOTHIAZOLE DERIVATIVES

(75) Inventor: Paul Spurr, Riehen (CH)

(73) Assignee: Hoffmann-La Roche Inc., Nutley, NJ (US)

(*) Notice: Subject to any disclaimer, the term of this patent is extended or adjusted under 35 U.S.C. 154(b) by 393 days.

(21) Appl. No.: 10/743,613

(22) Filed: Dec. 22, 2003

(65) Prior Publication Data

US 2004/0138465 A1 Jul. 15, 2004

(30) Foreign Application Priority Data

Jan. 7, 2003 (EP) .................... 03000048

(51) Int. Cl.
*C07D 277/82* (2006.01)
(52) U.S. Cl. ...................... 548/163; 548/164
(58) Field of Classification Search ............... 548/163, 548/164
See application file for complete search history.

(56) References Cited

U.S. PATENT DOCUMENTS

| 3,725,428 A | 4/1973 | Janiak |
| 4,028,374 A | 6/1977 | Pelosi, Jr. et al. |
| 5,099,021 A | 3/1992 | Worther et al. |
| 6,521,754 B1 | 2/2003 | Alanine et al. |

FOREIGN PATENT DOCUMENTS

DE 1953149 5/1970

(Continued)

OTHER PUBLICATIONS

Forlani, L. et al., *J. Heterocyclic. Chem.* vol. 37, 2000 pp. 63-69.

(Continued)

*Primary Examiner*—Kamal A. Saeed
(74) *Attorney, Agent, or Firm*—George W. Johnston; Patricia S. Rocha-Tramaloni; Kimberly K. Prior

(57) ABSTRACT

The present invention relates to a process for preparation of amino substituted benzothiazole derivatives of formula I

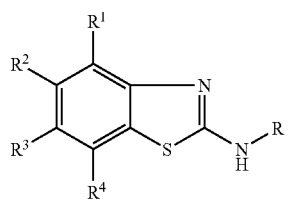

wherein
$R^1$, $R^2$ and $R^3$ are independently from each other hydrogen, lower alkyl, lower alkoxy or halogen;
$R^4$ is hydrogen, lower alkyl, lower alkyloxy, halogen, or is a five or six membered non aromatic heterocyclyl group, unsubstituted or substituted by lower alkyl or an oxo-group, or is —$NR^5R^6$, wherein $R^5$ and $R^5$ are independently from each other hydrogen, lower alkyl, —C(O)-lower alkyl, —$(CH_2)_n$O-lower alkyl or benzyl, opionally substituted by lower alkyl, or is an five or six membered heteroaryl group;

$R^1$ and $R^2$ or $R^2$ and $R^3$ may form together with the corresponding carbon atoms a ring containing —O—$CH_2$—O— or —CH=CH—CH=CH—;
R is hydrogen or —C(O)R';
R' is a five or six membered non aromatic heterocyclyl group, five or six membered heteroaryl group or is aryl, which rings may be substituted by the groups, selected from lower alkyl, halogen-lower alkyl, lower alkoxy, cyano, nitro, —C(O)H, —C(O)OH or by pyrrolidin-1-yl-methyl;
n is 1 to 4;
or a pharmaceutically acceptable salt thereof,
wherein the cyclization is carried out by the treatment of a compound of formula

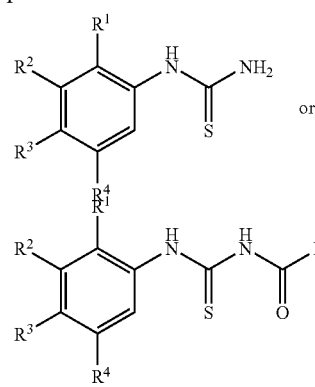

with sulphoxide/HBr/solvent to give the desired products of formula I for R is hydrogen (formula IA) or for R is —C(O)R' (formula IB)

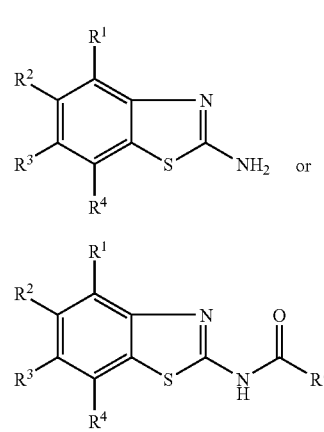

9 Claims, No Drawings

FOREIGN PATENT DOCUMENTS

| | | |
|---|---|---|
| EP | 0199400 A | 10/1986 |
| EP | 0 282 971 | 9/1988 |
| EP | 0 295 656 | 12/1988 |
| EP | 0 343 893 | 11/1989 |
| EP | 0 404 440 | 12/1990 |
| EP | 0 427 963 | 5/1991 |
| EP | 0 529 600 | 3/1993 |
| EP | 0 604 657 | 7/1994 |
| FR | 2 753 970 A | 4/1998 |
| GB | 1 345 552 A | 1/1974 |
| GB | 1 538 822 A | 1/1979 |
| WO | WO 99/37630 | 1/1999 |
| WO | WO 99/24035 | 5/1999 |
| WO | WO 00/18767 | 4/2000 |
| WO | WO 00/27819 A | 5/2000 |
| WO | WO 01/19360 A2 | 9/2000 |
| WO | WO 01/97786 | 12/2001 |

OTHER PUBLICATIONS

McDonald, F. et al., *Synthesis* 2000, No. 7, pp. 970-974.
Abstract corresponding to EP 0 529 600 (Document B3), Mar. 1993.
Colotta, V. et al., *Arch. Pharm. Med. Chem.*, 332 (1999) pp. 39-41.
Baraldi, P. G. et al., *J. Med. Chem.*, 39 (1996) pp. 1164-1171.
Li, A. H. et al., *J. Med. Chem.*, 42 (1999) pp. 706-721.
Kim, Y. C. et al., *J. Med. Chem.*, 41 (1998) pp. 2835-2845.
Li, A. H. et al., *J. Med. Chem.*, 41 (1998) pp. 3186-3201.
Baraldi, P. G. et al., *J. Med. Chem.*, 41 (1998) pp. 2126-2133.
Poulsen, S. A. et al., *Bioorganic & Medicinal Chemistry*, 6 (1998) pp. 619-641.
Müller, C. E. et al., *Bioorganic & Medicinal Chemistry*, 6 (1998) pp. 707-719.
Patent Abstracts of Japan, vol. 1999, No. 10, JP 11 130761a.
Pandeya, Surendra N. et al., *Indian Drugs* (1985), 23(3), 146-51 XP0080000199.
Daidone, G. et al., vol. 44, No. 5 (1989), pp. 465-473, XP001053114.
The Merck Index 12th Ed. (1996) p. 506.
Abstract corresponding to FR 2 753 970 (Document B9), 1998.
Abstract corresponding to WO 00/27819 (Document B12), 2000.
Carla Boga et al, Journal of the Chemical Society, Perkin Transactions 1, XP002296456, pp. 1363-1368 (1999).

CYCLIZATION PROCESS FOR SUBSTITUTED BENZOTHIAZOLE DERIVATIVES

FIELD OF THE INVENTION

The present invention relates to processes for the preparation of benzothiazole compounds.

BACKGROUND OF THE INVENTION

Compounds of formula I are described in WO 01/97786:

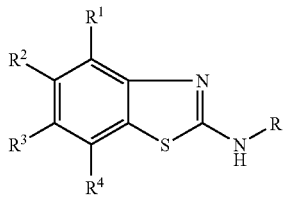

wherein $R^1$, $R^2$ and $R^3$ are independently from each other hydrogen, lower alkyl, lower alkoxy or halogen;

$R^4$ is hydrogen, lower alkyl, lower alkyloxy, halogen,
  or is a five or six membered non aromatic heterocyclyl group, unsubstituted or substituted by lower alkyl or an oxo-group, or is
  —$NR^5R^6$, wherein $R^5$ and $R^5$ are independently from each other hydrogen, lower alkyl, —C(O)-lower alkyl, —(CH$_2$)$_n$O-lower alkyl or benzyl, optionally substituted by lower alkyl, or is a five or six membered heteroaryl group;

$R^1$ and $R^2$ or $R^2$ and $R^3$ may form together with the corresponding carbon atoms a ring containing —O—CH$_2$—O— or —CH═CH—CH═CH—;

R is hydrogen or —C(O)R';

R' is a five or six membered non aromatic heterocyclyl group, five or six membered heteroaryl group or is aryl, which rings may be substituted by the groups, selected from lower alkyl, halogen-lower alkyl, lower alkoxy, cyano, nitro, —C(O)H, —C(O)OH or by pyrrolidin-1-yl-methyl;

n is 1 to 4;

or a pharmaceutically acceptable salt thereof.

In particular, WO 01/97786 describes compounds of formulas IA and IB

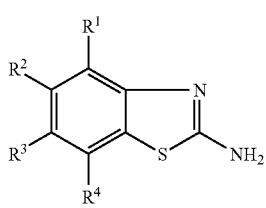

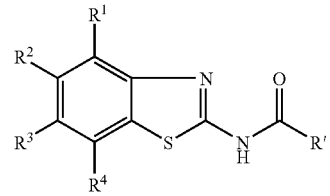

Compounds of formula IA may be used as intermediates for the preparation of compounds of formula IB, which compounds are pharmaceutically active as adenosine receptor ligands.

Compounds of formula IB are important in the regulation of many aspects of cellular metabolism and in the modulation of different central nervous system activities. As such, the compounds of formula IB may be used in the control or prevention of illnesses based on the modulation of the adenosine system, such as Alzheimer's disease, Parkinson's disease, neuroprotection, schizophrenia, anxiety, pain, respiration deficits, depression, asthma, allergic responses, hypoxia, ischaemia, seizure and substance abuse. Furthermore, compounds of the present invention may be useful as sedatives, muscle relaxants, antipsychotics, antiepileptics, anticonvulsants and cardioprotective agents. The most preferred indications for compounds of formula IB are those, which are based on the $A_{2A}$ receptor antagonistic activity and which include disorders of the central nervous system, for example the treatment or prevention of certain depressive disorders, neuroprotection and Parkinson's disease. The compounds are further useful in the treatment of diabetes mellitus, obesity and ADHD (attention deficit hyperactivity disorder).

In general, the preparation of compounds of formula I, wherein R is hydrogen, is well known. For example, in WO 01/97786 the following process is described:

Scheme 1

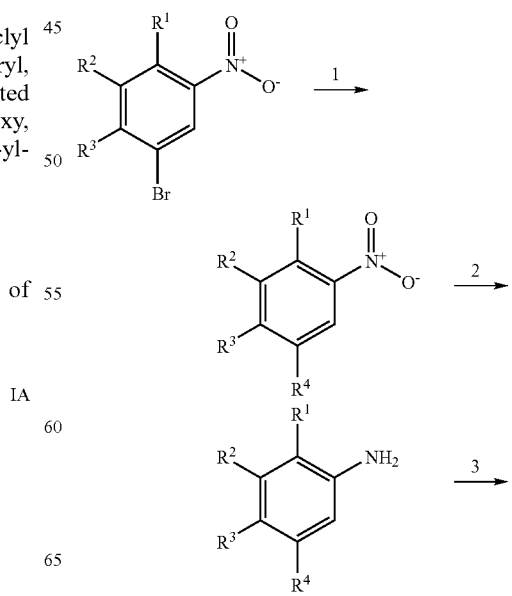

-continued

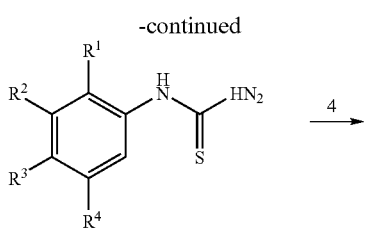

IA wherein the numbers 1–4 have the following meaning:
1 HR$^4$, Pd(OAc)$_2$, BDCP, K$_3$PO$_4$, DME (ethylene glycol dimethl ether), 80° C./24 h/90%;
2 H$_2$, Pd—C, EtOH/CH$_2$Cl$_2$, RT/12 h/95%;
3 PhCONCS, acetone, RT/30 min/95% and NaOMe, MeOH, RT/2 h/90%;
4 SOCl$_2$, 55° C./10 min/75%;

BDCP is

The definition of substituents is described above.

It has been shown that most of the starting materials and the ligand are very expensive and only available in small quantities, and the cyclization step could not be scaled up without resorting to chromatography.

Another way to produce amino-benzothiazoles is described in EP 282971 as follows:

Scheme 2

It has been shown that this reaction step often leads to amino-benzothiazoles in low yields due to competing reactions.

EP 529 600 describes a process for preparation of amino-benzothiazoles comprising the following step:

Scheme 3

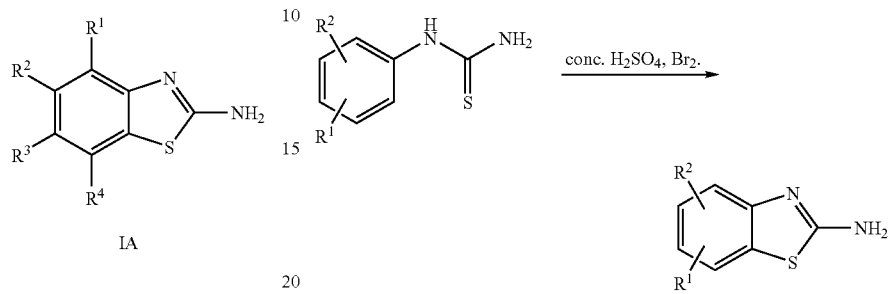

It has been shown that the reaction variants, conducted according to literature precedent, such as Br$_2$/CHCl$_3$ or AcOH, I$_2$/MeOH or SOCl$_2$/CHCl$_3$ are often not suitable for the preparation of amino-benzothiazoles, especially in large amounts.

Due to the relative high electron density within the amino-substituted phenyl ring in some specific cases required for the present purposes, competing reactions on this ring before or after cydization always occurred to a certain extents. Other approaches such as the use of aq NH$_4$Br and H$_2$SO$_4$ (EP 529600) or treating the aniline directly with NaSCN/Br$_2$/AcOH (*Synthesis*, 970, 31, 2000) failed to offer any improvement.

A more subtle way of activating the thione sulphur atom was found in the acid catalyzed transfer oxidation of thioureas with DMSO (*J. Heterocyclic Chem.*, 63, 37, 2000). But in the absence of suitable trapping agents a dimerization reaction took place to give undesired iminothiadiazoles.

All methods, described in the literature, do not give the desired end products of formula IA and IB in good yields without unpredictable side products.

SUMMARY OF THE INVENTION

Therefore, it is an object of the present invention to provide a cyclization process for the preparation of benzothiazole derivatives of formula I for R=hydrogen (formula IA) and for R=—C(O)R' (formula IB), in good yields and with minimal side products.

IA or

-continued

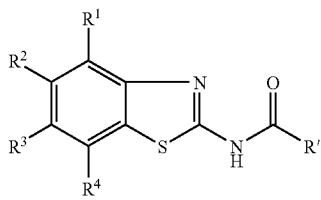

IB wherein
R¹, R² and R³ are independently from each other hydrogen, lower alkyl, lower alkoxy or halogen;
R⁴ is hydrogen, lower alkyl, lower alkyloxy, halogen,
or is a five or six membered non aromatic heterocyclyl group, unsubstituted or substituted by lower alkyl or an oxo-group, or is
—NR⁵R⁶, wherein R⁵ and R⁵ are independently from each other hydrogen, lower alkyl, —C(O)-lower alkyl, —(CH₂)ₙO-lower alkyl or benzyl, optionally substituted by lower alkyl, or is a five or six-membered heteroaryl group;
R¹ and R² or R² and R³ may form together with the corresponding carbon atoms a ring containing —O—CH₂—O— or —CH=CH—CH=CH—;
R' is a five or six membered non aromatic heterocyclyl group, five or six membered heteroaryl group or is aryl, which rings may be substituted by the groups, selected from lower alkyl, halogen-lower alkyl, lower alkoxy, cyano, nitro, —C(O)H, —C(O)OH or by pyrrolidin-1-yl-methyl;
n is 1 to 4;

or a pharmaceutically acceptable salt thereof.

DESCRIPTION OF THE INVENTION

As used herein, the term "lower alkyl" denotes a saturated straight- or branched-chain alkyl group containing from 1 to 6 carbon atoms, for example, methyl, ethyl, propyl, isopropyl, n-butyl, i-butyl, 2-butyl, t-butyl and the like. Preferred lower alkyl groups are groups with 1–4 carbon atoms.

The term "halogen" denotes chlorine, iodine, fluorine and bromine.

The term "lower alkoxy" denotes a group wherein the alkyl residues are as defined above, and which is attached via an oxygen atom.

The term "five or six membered heteroaryl" denotes the following groups: pyrrol-1-yl, tetrazolyl, imidazol-1 or 2-yl, pyrazol1-yl, pyridin-1, 2, 3 or 4-yl, pyrazinyl, pyrimidinyl, pyridazinyl, isothiazolyl, isoxazolyl, thienyl or furyl;

The term "five or six membered non aromatic heterocycyl" denotes the following groups: pyrrolidinyl, hydropyranyl, imidazolidinyl, pyrazolidinyl, piperidinyl, piperazinyl, morpholinyl, thiomorpholinyl, thiomorpholin-1,1-dioxo or thiomorpholin-1-oxo.

The term "aryl" denotes phenyl, benzyl or naphthyl.

The term "pharmaceutically acceptable salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

The present invention provides a cyclization process for the preparation of benzothiazole derivatives of formula I for R=hydrogen (formula IA) and for R=—C(O)R' (formula IB), in good yields and with minimal sideproducts.

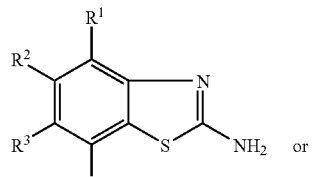

IA or

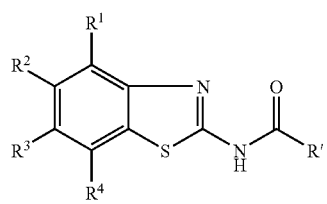

IB wherein
R¹, R² and R³ are independently from each other hydrogen, lower alkyl, lower alkoxy or halogen;
R⁴ is hydrogen, lower alkyl, lower alkyloxy, halogen,
or is a five or six membered non aromatic heterocyclyl group, unsubstituted or substituted by lower alkyl or an oxo-group, or is
—NR⁵R⁶, wherein R⁵ and R⁵ are independently from each other hydrogen, lower alkyl, —C(O)-lower alkyl, —(CH₂)ₙO-lower alkyl or benzyl, optionally substituted by lower alkyl, or is a five or six membered heteroaryl group;
R¹ and R² or R² and R³ may form together with the corresponding carbon atoms a ring containing —O—CH₂—O— or —CH=CH—CH=CH—;
R' is a five or six membered non aromatic heterocyclyl group, five or six membered heteroaryl group or is aryl, which rings may be substituted by the groups, selected from lower alkyl, halogen-lower alkyl, lower alkoxy, cyano, nitro, —C(O)H, —C(O)OH or by pyrrolidin-1-yl-methyl;
n is 1 to 4;

or a pharmaceutically acceptable salt thereof.

The process of the invention comprises treating compounds of formulas

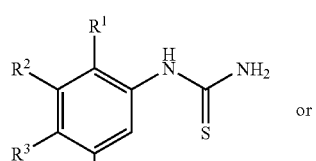

II or

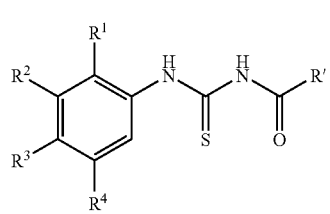

III with sulphoxide/HBr/solvent gave the desired products of formulas

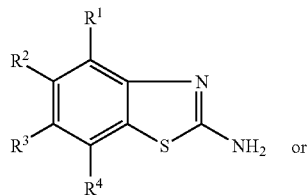

IA

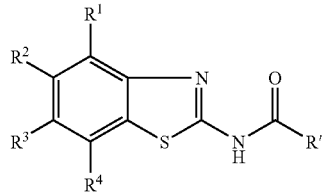

IB in a good yield of up to 90% and with minimal or no side reactions.

As a sulphoxide, for example, DMSO is suitable, since it is commercially available, cheap and non-toxic.

HBr may be used in any form, including gaseous, or for example in form of an in situ prepared bromide salt and a strong acid. Suitable is HBr—AcOH, since this represents a convenient form of 'liquid' concentrated HBr.

As a solvent maybe used, for example, $CH_2Cl_2$, $CH_3CN$, THF, AcOH or EtOAc.

Preferred solvents are AcOH or EtOAc.

In more detail, the reactions may be described as follows:

Scheme 4

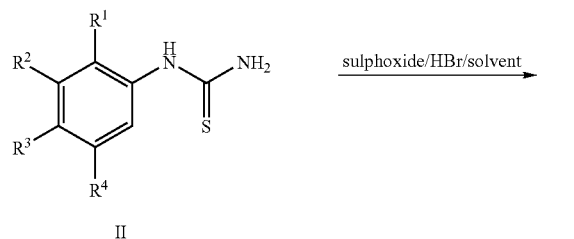

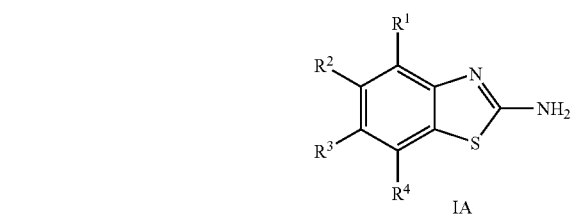

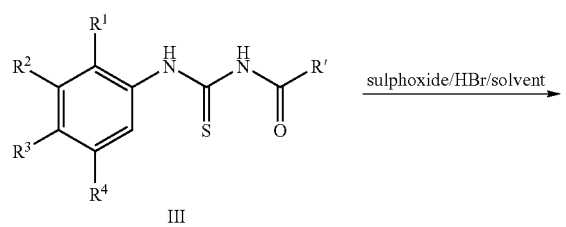

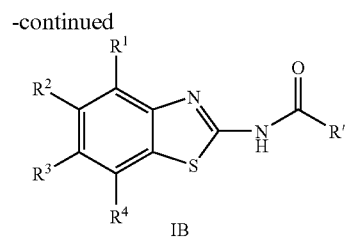

IB

A thiourea of formula II or III is suspended with vigorous stirring in ethyl acetate (EtOAc) at 80° C. Hydrogen bromide (HBr=33%) in acetic acid is added dropwise within 0.2 h, followed by the addition of dimethylsulfoxide in one portion. The suspension is refluxed for 4 h. Then the reaction mixture is cooled to RT and after 0.2 h is filtered. The product is washed portionwise with ethyl acetate. The aminobenzothiazole IA or the corresponding benzamide of formula IB is then purified by liberating it from the crude HBr-salt. This is dissolved in ethanol, diluted with water and heated to 55° C. The obtained solution is basified with aqueous ammonia to pH 9–10, forming a suspension which is stirred and allowed to cool to RT overnight (16 h). The products are filtered and washed portionwise with aqueous ethanol and then dried for 24 h at 45° C. Yield ~90%.

Furthermore, it has been shown that the treatment of a thiourea of formulas II or III with DMSO/HBr/AcOH delivered the desired product of formula IA or IB (yield: ~60–80%), but always accompanied by unpredictable amounts of iminothiazoles (~5–25%). The formation of the side product was attributed to the partial solubility of the protonated thioureas of formula II or III in hot AcOH. Aqueous HBr was also effective, but induced some thiourea-urea transformation. Two equivalents of HBr was necessary for complete conversion in the cases where a basic unit was attached to the aryl-ring. The reaction proceeded best at >70° C., but was rapid and fairly exothermic at this temperature. The starting material quickly dissolved upon DMSO addition and the product almost completely precipitated immediately thereafter.

It has been found that after cooling and filtration, the benzothiazoles of formulas IA or IB may be isolated in good purity. By conducting the reaction entirely in EtOAc, the problem of competitive dimerization was finally overcome since the HBr-salts of both reactant and product were barely soluble in this solvent thus averting all further side reactions.

The compounds of formula IA may be used for the preparation of end-products of formula IB as described in the following scheme:

Scheme 5

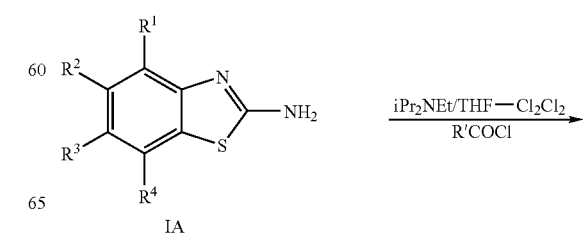

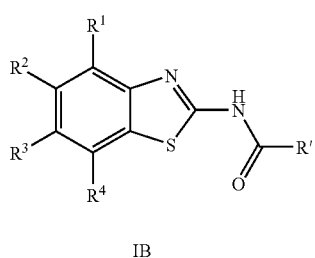

IB

This reaction is described in more detail in WO 01/97786.

The starting compounds of formulas II and III may be prepared as described in the above scheme:

Compounds of formula III maybe prepared as follows:

A compound of formula IV is dissolved in sulphuric acid, maintaining a temperature between 0–10° C. The obtained solution is cooled to ca. −5° C. In a separate flask, nitric acid is added to sulphuric acid and precooled to ca. 10° C. This mixture is then added the above solution within 1 h ensuring that the temperature remained <0° C. The reaction mixture is quenched into ice and to the aqueous solution aqueous ammonia is added. The suspension is diluted with water and stirred at RT for 0.2 h before being filtered. The obtained product of formula V is washed with water and dried. This compound is then suspended in methanol, and dichloromethane is added to generate a solution. Pd—C is added, and the reduction is commenced at RT under hydrogen with stirring. The reaction is complete after 1.5 h. The mixture is filtered, the residue is rinsed with MeOH, and the filtrate is concentrated under reduced pressure. Water is added, and

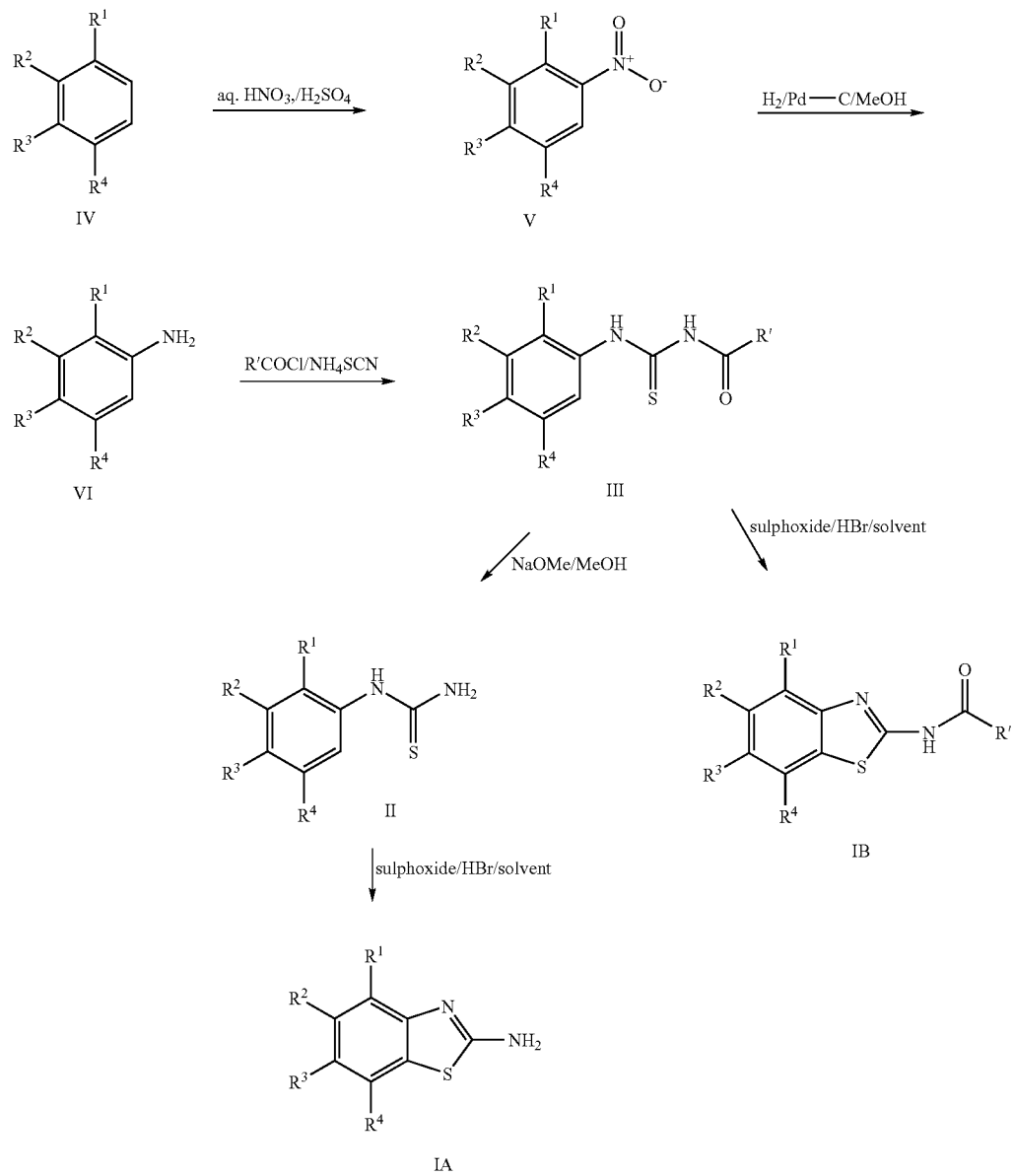

the resulting suspension is heated again to 60° C. to remove residual MeOH. The obtained product of formula VI is filtered, washed with aqueous MeOH and dried.

Ammonium thiocyanate is dissolved in acetone at RT, and benzoyl chloride is added to create PhCONCS in situ. The reaction mixture is heated to reflux and then treated with a warm solution of a compound of formula VI in acetone over 0.25 h. After 2.5 h, the solvent is removed by distillation at ambient pressure with the continuous addition of water. After cooling the suspension to RT, the product of formula III is filtered, washed with water and dried.

The benzoylthiourea of formula III is suspended in methanol at RT, and sodium methoxide is added over 0.75 h. The suspension is stirred for 2.75 h. The reaction mixture is cooled to ~0° C. and stirred for 1 h before being filtered. The obtained product of formula II is washed with methanol and dried. The further conversion of compounds of formula III to IB and II to IA is described above.

The following examples are described to illustrate the present invention without limiting it. RT is room temperature.

EXAMPLE 1

N-(4-Methoxy-7-morpholin-4-yl-benzothiazol-2-yl)-2-methyl-isonicotinamide a) 4-(4-Methoxy-3-nitro-phenyl)-morpholine

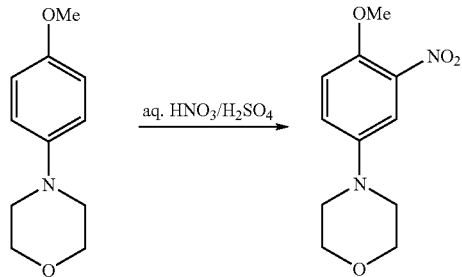

60.0 g Arylmorpholine (0.31 mol) were dissolved in 273 ml 95% sulphuric acid (4.84 mol, 15.6 eq.), while maintaining a temperature between 0–10° C. Stirring at 10° C. was continued for 0.5 h to produce a brown solution which was cooled to ca. −5° C. In a separate flask, 20.9 ml 65% nitric acid (0.34 mol, 0.98 eq.) were added to 30 ml 95% sulphuric acid (0.53 mol, 1.7 eq) precooled to ca. 10° C. This nitrating mixture was then added to the above solution within 1 h ensuring that the temperature remained <0° C. The dark brown reaction mixture was then worked up in a conventional manner (70 g, ~95%). The crude product was sufficiently pure to be used directly in the next step.

b) 2-Methoxy-5-morpholin-4-yl-phenylamine

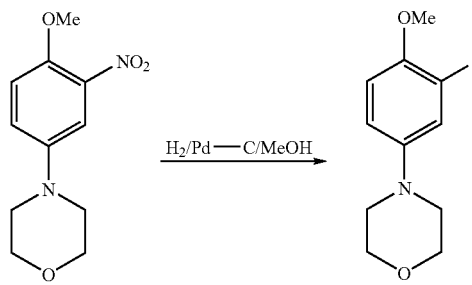

40.2 g Nitroanisole (0.169 mmol) were suspended in 402 ml methanol, and 65 ml dichloromethane were added to generate a solution. 2.0 g 5% Pd—C were added, and the reduction was commenced at RT under hydrogen. The reaction was complete after 1.5 h. The reaction mixture was then worked up in a conventional manner. The crude product was sufficiently pure to be used directly in the next step. 32.8 g (93%).

c) 1-Benzoyl-3-(2-methoxy-5-morpholin-4-yl-phenyl)-thiourea

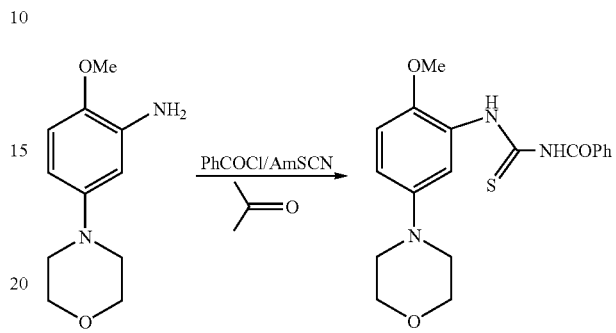

13.1 g Ammonium thiocyanate (AmSCN) (142 mmol, 1.1 eq.) were dissolved in 135 ml acetone at RT. 22.7 g. Benzoyl chloride (160 mmol, 1.02 eq.) were added in one portion. The reaction mixture was heated to reflux (~60° C.) for 0.5 h and then treated with a warm (~40° C.) solution of 32.5 g the aniline (156 mmol) in 260 ml acetone over 0.25 h. The heating was continued for 2.5 h. The work-up was carried out in conventional manner. The crude product was sufficiently pure to be used directly in the next step. 54.8 g (94%).

d) (2-Methoxy-5-morpholin-4-yl-phenyl)-thiourea

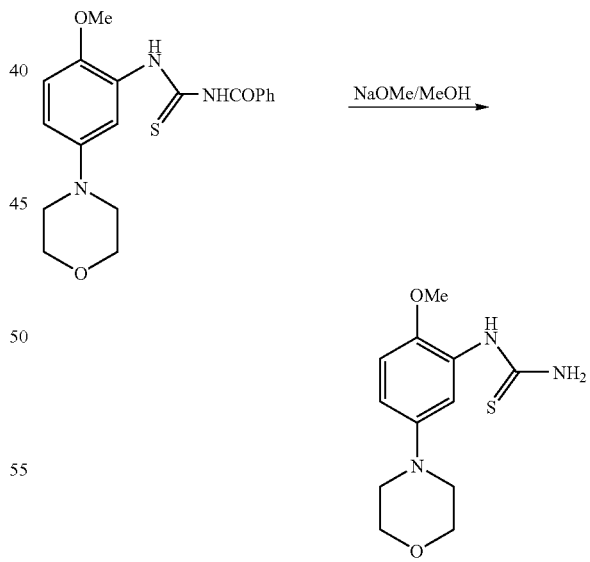

212 g Benzoylthiourea (571 mmol) were suspended in 1270 ml methanol at RT, and 155 ml 30% methanolic sodium methoxide (861 mmol, 1.5 eq.) were added over 0.75 h. The suspension was stirred for 2.75 h, cooled to ~0° C. and stirred for 1 h before being filtered. The crude product was sufficiently pure to be used directly in the next step. 148.7 g (97%).

e) 4-Methoxy-7-morpholin-4-yl-benzothiazol-2-ylamine

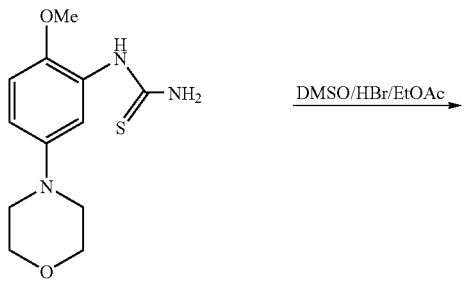

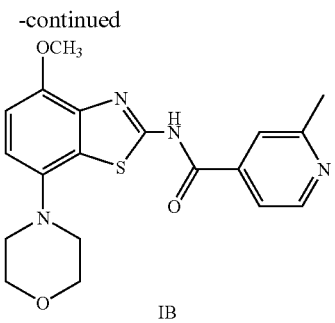

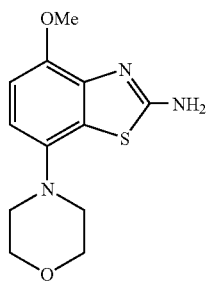

50 g (187 mmol) thiourea were suspended with vigorous stirring in 560 ml ethyl acetate. The light grey suspension was brought to reflux, and 1.8 g hydrogen bromide (33% in acetic acid, 65.5 ml, 374 mmol, 2.0 eq.) were added dropwise within 0.2 h, followed by, 0.2 h later, 17.5 g dimethylsulfoxide (224 mmol, 15.9 ml, 1.2 eq.) in one portion. The suspension was refluxed for 4 h, during which the colour changed from dark to light yellow. The reaction mixture was cooled to RT and, after 0.2 h, was filtered. The product was washed portionwise with 190 ml ethyl acetate.

The aminobenzothiazole was purified by liberating it from the undried crude HBr-salt. This was dissolved in 450 ml ethanol, diluted with 600 ml water and heated to 55° C. The red solution was basified with 50 ml 25% aqueous ammonia to pH 9–10, forming a suspension which was stirred and allowed to cool to RT overnight (16 h). The product was filtered and washed portionwise with 140 ml 50% aqueous ethanol and then dried for 24 h at 45° C./1 mb. 45.1 g (90%)

$^1$H-NMR: (400 MHz, CDCl$_3$): δ=3.05 (m, 4H), 3.86 (m, 4H), 3.95 (s, 3H), 5.14 (bs, 2H), 6.73 (d, 2H), 6.78 (d, 2H). MS: 266 (M+H$^+$).

f) N-(4-Methoxy-7-morpholin-4-yl-benzothiazol-2-yl)-2-methyl-isonicotinamide

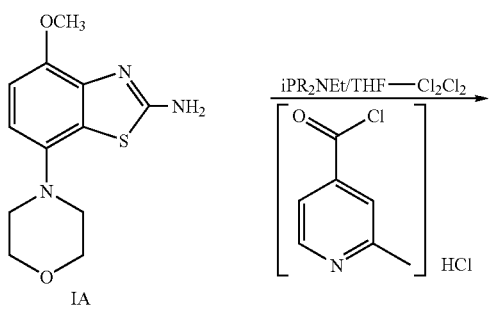

20.0 g Pyridine acid (115 mmol) were suspended at RT in 100 ml dichloromethane. 0.5 ml Dimethylformamide (6.5 mmol) was added, and after 0.2 h, 14.9 g oxalyl chloride (10.2 ml, 115 mmol) were added over 2 min. The dropping funnel was rinsed with 4 ml dichloromethane. The brown suspension was stirred at RT for 3 h. Then 200 ml tetrahydrofuran were added causing the acid chloride to partially precipitate. After 0.2 h, 24.3 g aminobenzothiazole (IA) (92 mmol) were added in one portion at RT. Directly afterwards, 56.0 ml N-ethyldiisopropylamine (42 g, 321 mmol) were added over 0.1 h., and the reaction mixture was stirred at RT overnight (~17 h). The contents were heated to reflux (~60° C.), and 300 ml water were added whilst maintaining ca. constant volume throughout a distillation process until the internal temperature reached 90° C. Once all the water was added, heating was increased to 110° C. and a total of 280 ml of distillate was collected. A further 320 ml water was added in one portion, and the temperature was increased to 120° C. whereby the internal and distillate temperature rose to ~70° C.

Around 20 ml more solvent was removed, and after 0.1 h, the internal and distillate temperatures reached 90° and 75° C., respectively. The reaction contents were allowed to cool to RT (ca. 1.2 h); then stirring was continued for 1.5 h to complete the precipitation of the product. This product was filtered and washed in 30 ml portions with a total of 150 ml water. Further purification was carried out in conventional manner. Yield: 30.4 g (86% from amine).

EXAMPLE 2

N-(7-Acetylamino-4-methoxy-benzothiazol-2-yl)-benzamide

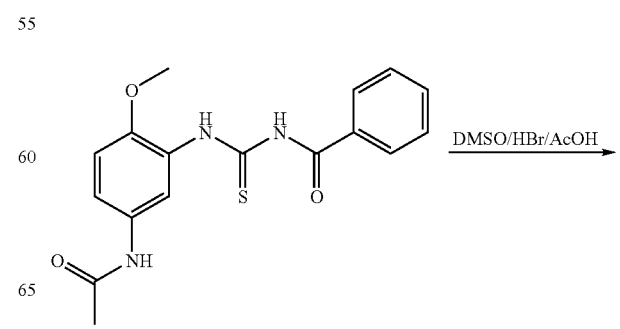

-continued

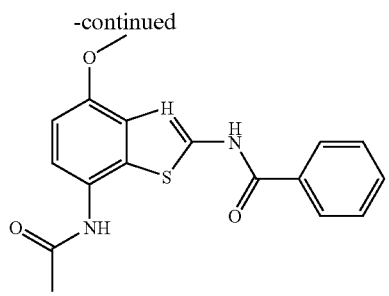

To a suspension of 15.0 g (43.7 mmol) N-[3-(3-benzoyl-thioureido)-4-methoxy-phenyl]-acetamide in 200 ml glacial acetic acid was added 7.65 ml (43.6 mmol) of a 5.7 M solution of HBr in acetic acid, and the mixture was heated at 90° C. for 1 h. 2.5 ml (48.0 mmol) DMSO was then added, and stirring continued at 90° C. for 1.5 h. After cooling to room temperature, the reaction mixture was poured onto 1000 ml distilled water, and the resulting slurry stirred for 15 min. The mixture was then filtered, and the filter cake washed with water, then dried in vacuo at 50° C., affording 12.8 g (86%) N-(7-acetylamino-4-methoxy-benzothiazol-2-yl)-benzamide as a light brown solid. ES-MS m/e (%): 342 (M+H$^+$, 100).

In an analogous manner there were obtained:

EXAMPLE 3

4-(2-Amino-4-methoxy-benzothiazol-7-yl)-1-methyl-piperazin-2-one

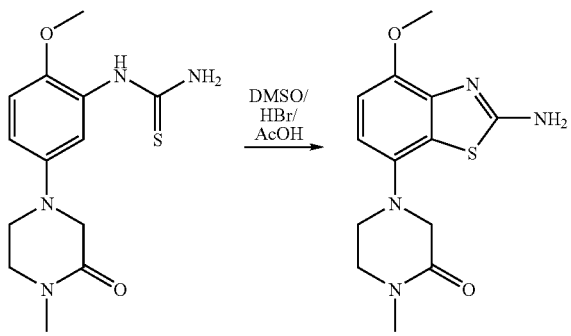

From [2-methoxy-5-(4-methyl-3-oxo-piperazin-1-yl)-phenyl]-thiourea with HBr—AcOH (4 equiv.) and DMSO (2.4 equiv.) in AcOH. ES-MS m/e (%): 293 (M+H$^+$, 100).

EXAMPLE 4

N-{7-[Bis-(4-methyl-benzyl)-amino]-4-methoxy-benzothiazol-2-yl}-benzamide

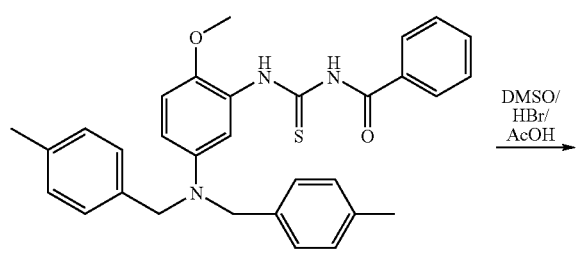

-continued

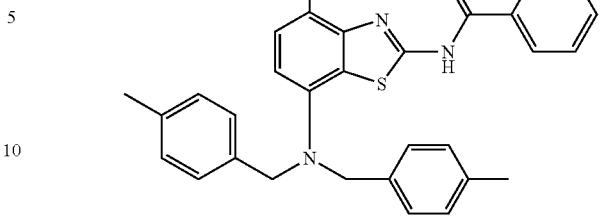

From 1-benzoyl-3-{5-[bis-(4-methyl-benzyl)-amino]-2-methoxy-phenyl}-thiourea with HBr—AcOH (2 equiv.) and DMSO (1.1 equiv.) in AcOH. ES-MS m/e (%): 508 (M+H$^+$, 100).

EXAMPLE 5

N-{4-Methoxy-7-[(2-methoxy-ethyl)-methyl-amino)]-benzothiazol-2-yl}-benzamide

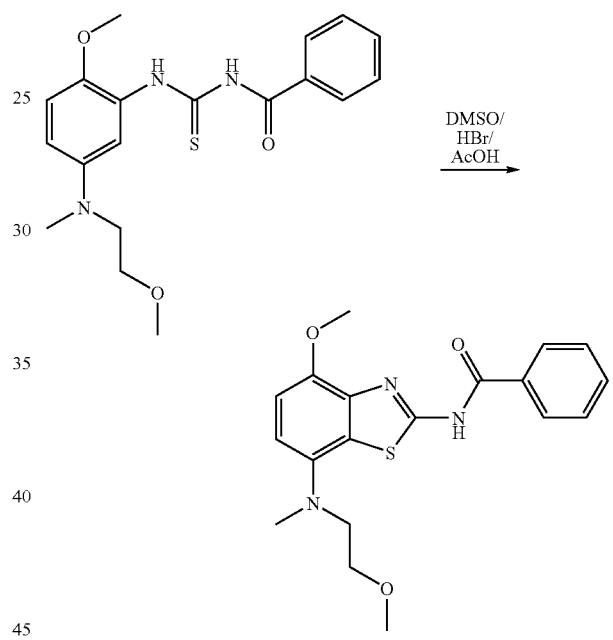

From 1-benzoyl-3-{2-methoxy-5-[(2-methoxy-ethyl)-methyl-amino]-phenyl}-thiourea with HBr—AcOH (2 equiv.) and DMSO (1.1 equiv.) in AcOH. ES-MS m/e (%): 372 (M+H$^+$, 100).

EXAMPLE 6

4-Methoxy-N7-(2-methoxy-ethyl)-N7-methyl-benzothiazole-2,7-diamine

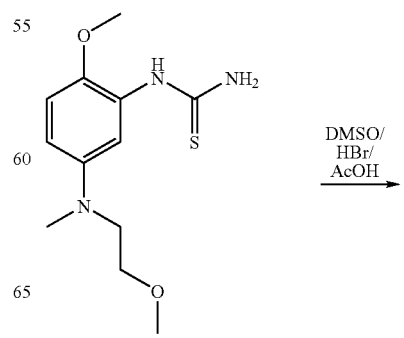

-continued

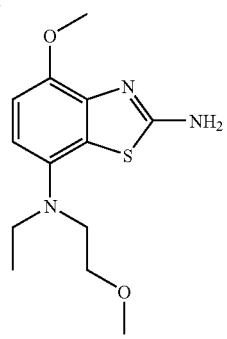

From {2-methoxy-5-[(2-methoxy-ethyl)-methyl-amino]-phenyl}-thiourea with HBr—AcOH (2 equiv.) and DMSO (1.1 equiv.) in AcOH. ES-MS m/e (%): 268 (M+H$^+$, 100).

EXAMPLE 7

2-Amino-6-methyl-benzothiazole

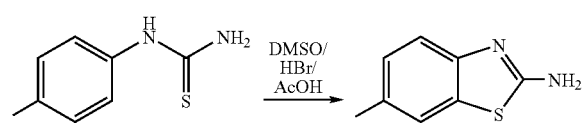

(4-Methylphenyl)thiourea (2 mmol) was added to AcOH (4 ml), and the suspension was heated to 80° C. To the solution formed was added 33% HBr in AcOH (4 mmol) followed by DMSO (2.1 mmol). After stirring at 80° C. for 1 h, the reaction mixture was cooled to 50° C., diluted with EtOAc (10 ml) and filtered. The product (as HBr-salt) was taken up in H$_2$O (5 ml) and treated with 1M aq. NaHCO$_3$ (2 ml). Stirring was continued for 0.2 h. The precipitated aminobenzothiazole was then filtered, washed with H$_2$O (10 ml) and dried (16 h at 45° C./20 mb); yield 67%.

$^1$H-NMR (400 MHz, DMSO-d$_6$): δ=2.31 (s, 3H, CH$_3$), 7.00 (d, 1H, ArH-5), 7.21 (d, 1H, ArH-4), 7.31 (bs, 2H, NH$_2$), 7.44 (s, 1H, ArH-7). MS: 165 (M+H$^+$).

EXAMPLE 8

4-Methoxy-7-(tetrahydro-pyran-4-yl)-benzothiazol-2-ylamine

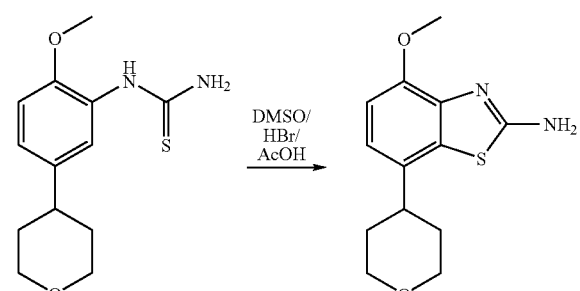

[2-Methoxy-5-(tetrahydropyran-4-yl)-phenyl]-thiourea was treated in the same manner as in Example 7; yield 64%.

$^1$H-NMR: (400 MHz, DMSO-d$_6$): δ=1.74 (m, 4H), 2.68 (m, 1H), 3.45 (m, 2H), 3.82 (s, 3H), 3.95 (m, 2H), 6.84 (d, 2H), 6.89 (d, 2H), 7.62 (bs, 1H). MS: 265 (M+H$^+$).

EXAMPLE 9

N-(4-Methyl-benzothiazol-2-yl)-benzamide

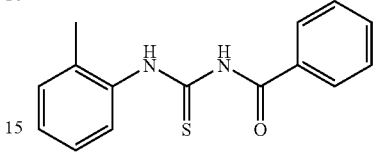

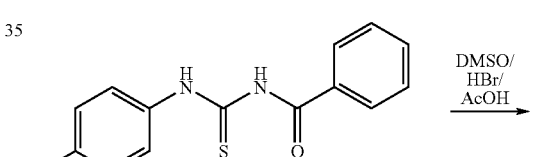

Benzoyl-3-o-tolyl-thiourea was treated in the same manner as in Example 7; yield 52%.

$^1$H-NMR (400 MHz, DMSO-d$_6$): δ=2.64 (s, 3H, CH$_3$), 7.26 (m, 2H), 7.57 (m, 2H), 7.67 (m, 1H), 7.83 (dd, 1H), 8.15 (dd, 1H), 12.9 (bs, 1H). MS: 269 (M+H$^+$).

EXAMPLE 10

N-(6-Methyl-benzothiazol-2-yl)-benzamide

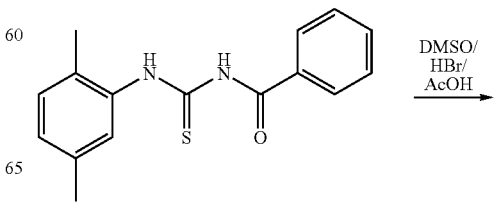

Benzoyl-3-p-tolyl-thiourea was treated in the same manner as in Example 7; yield 37%.

$^1$H-NMR (400 MHz, DMSO-d$_6$): δ=2.44 (s, 3H, CH$_3$), 7.29 (dd, 1H), 7.57 (m, 2H), 7.67 (m, 2H), 7.81 (d, 1H), 8.13 (m, 2H), 12.7 (bs, 1H). MS: 269 (M+H$^+$).

EXAMPLE 11

N-(4,7-Dimethyl-benzothiazol-2-yl)-benzamide

-continued

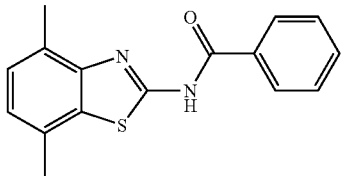

Benzoyl-3-(2,5-dimethyl-phenyl)-thiourea was treated in the same manner as in Example 7; yield 76%. MS: 283 (M+H⁺).

EXAMPLE 12

N-(5,7-Dimethyl-benzothiazol-2-yl)-benzamide

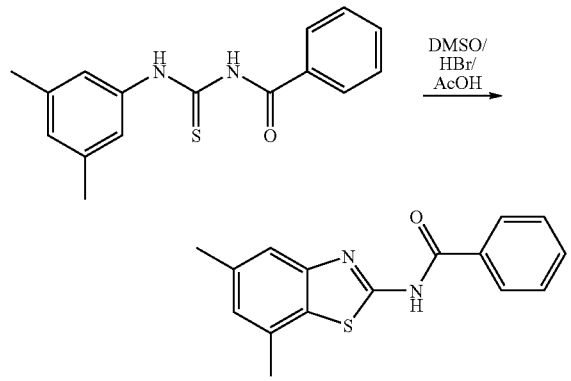

Benzoyl-3-(3,5-dimethyl-phenyl)-thiourea was treated in the same manner as in Example 7; yield 83%. MS: 283 (M+H⁺).

EXAMPLE 13

N-(4-Nitro-7-methyl-benzothiazol-2-yl)-benzamide

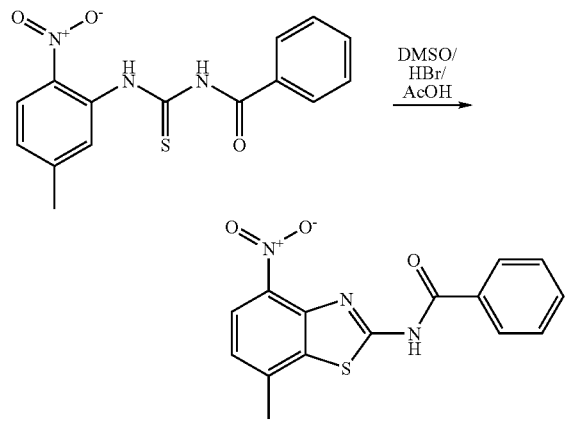

1-(2-Nitro-5-methyl-phenyl)-3-benzoyl-thiourea was treated in the same manner as in Example 7; yield 34%.

¹H-NMR (400 MHz, DMSO-d₆): δ=2.67 (s, 3H, CH₃), 7.36 (d, 1H), 7.59 (m, 2H), 7.70 (m, 1H), 8.14 (d, 1H), 8.18 (m, 2H), 13.4 (bs, 1H). MS: 314 (M+H⁺), 336 (M+Na⁺).

EXAMPLE 14

N-(4-Methoxy-7-morpholin-benzothiazol-2-yl)-benzamide

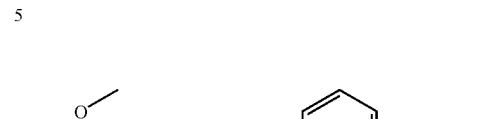

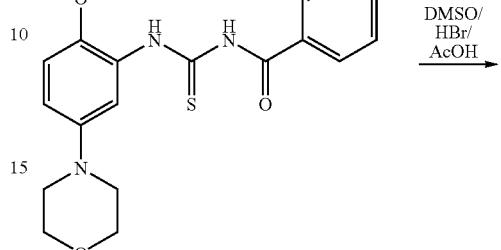

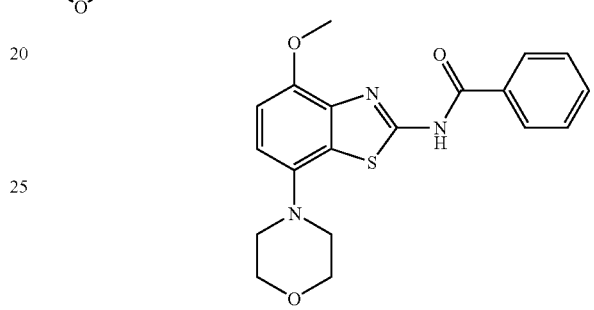

Benzoyl-3-(2-methoxy-5-morpholin-4-yl-phenyl)-thiourea was treated in CH₂Cl₂ (5 ml) in the same manner as in Example 7. An extractive work-up with CH₂Cl₂/aq. NaHCO₃ provided the crude product which was triturated in TBME (4 ml) at 50° C., cooled to RT and filtered; yield 68%.

¹H-NMR: (400 MHz, CDCl₃): δ=3.08 (m, 4H), 3.80 (s, 3H), 3.86 (m, 4H), 6.73 (d, 2H), 6.83 (d, 2H), 7.44 (m, 2H), 7.56 (m, 1H), 7.88 (d, 2H). MS: 370 (M+H⁺), 392 (M+Na⁺).

EXAMPLE 15

N-(5,7-Dimethoxy-benzothiazol-2-yl)-benzamide

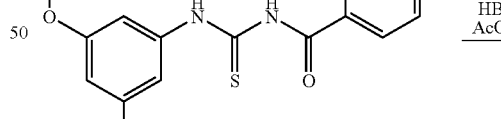
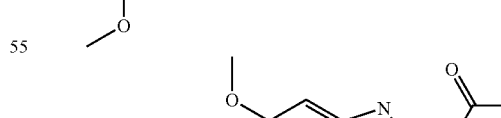
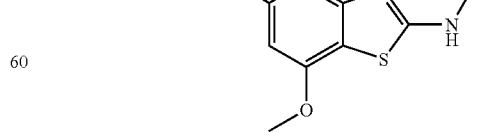

Benzoyl-3-(3,5-dimethoxy-phenyl)-thiourea was treated in the same manner as in Example 7; yield 90%. MS: 315 (M+H⁺).

EXAMPLE 16

N-Naphtho [2,1-d]thiazol-2-yl-benzamide

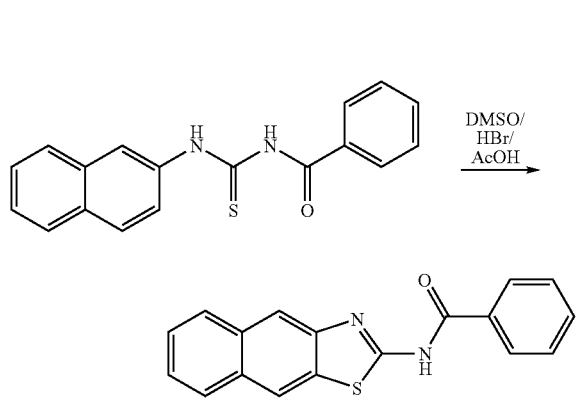

Benzoyl-3-naphthalen-2-yl-thiourea was treated in the same manner as in Example 7; yield 96%.

$^1$H-NMR: (400 MHz, DMSO-d$_6$): δ=7.60 (m, 3H), 7.67 (m, 2H), 7.93 (d, 1H), 7.99 (d, 1H), 8.10 (m, 2H), 8.18 (m, 2H), 13.0 (bs, 1H). MS: 305 (M+H$^+$).

The invention claimed is:

1. A process for preparation of amino substituted benzothiazole derivatives of formula I

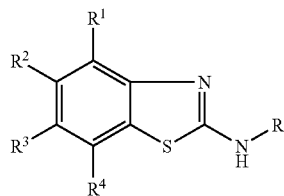

wherein
- R$^1$, R$^2$ and R$^3$ are independently from each other hydrogen, lower alkyl, lower alkoxy or halogen;
- R$^4$ is hydrogen, lower alkyl, lower alkyloxy, halogen, or is a five or six membered non aromatic heterocyclyl group, unsubstituted or substituted by lower alkyl or an oxo-group, or is
- —NR$^5$R$^6$, wherein R$^5$ and R$^5$ are independently from each other hydrogen, lower alkyl, —C(O)-lower alkyl, —(CH$_2$)$_n$O-lower alkyl or benzyl, optionally substituted by lower alkyl, or is a five or six membered heteroaryl group;
- R$^1$ and R$^2$ or R$^2$ and R$^3$ may form together with the corresponding carbon atoms a ring containing —O—CH$_2$—O— or —CH═CH—CH═CH—;
- R is hydrogen or —C(O)R';
- R' is a five or six membered non aromatic heterocyclyl group, five or six membered heteroaryl group or is aryl, which rings may be substituted by the groups, selected from lower alkyl, halogen-lower alkyl, lower alkoxy, cyano, nitro, —C(O)H, —C(O)OH or by pyrrolidin-1-yl-methyl;
- n is 1 to 4;
- or a pharmaceutically acceptable salt thereof,
- wherein the cyclization is carried out by the treatment of a compound of formula

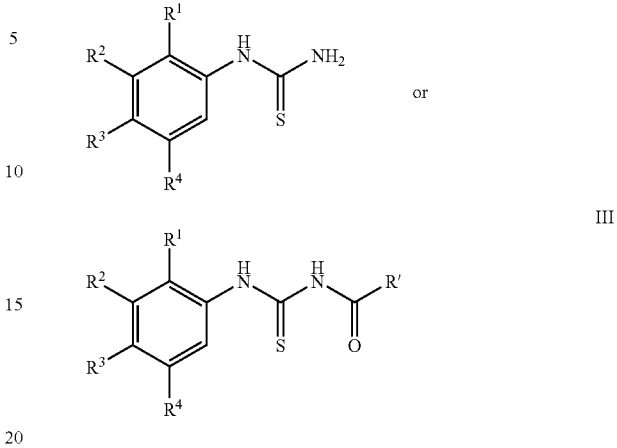

with sulphoxide/HBr/solvent to give the desired products of formula I for R is hydrogen (formula IA) and for R is —C(O)R' (formula IB)

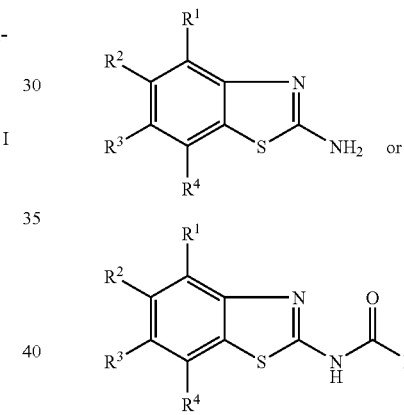

2. The process in accordance with claim 1, wherein the sulphoxide is dimethyl sulphoxide.

3. The process in accordance with claim 1, wherein HBr is an in situ prepared bromide salt and a strong acid.

4. The process in accordance with claim 3, wherein the in situ prepared bromide salt and the strong acid is HBr—AcOH.

5. The process in accordance with claim 1, wherein the solvent is CH$_2$Cl$_2$, CH$_3$CN, THF, AcOH or EtOAc.

6. The process in accordance with claim 5, wherein the solvent is AcOH or EtOAc.

7. The process in accordance with claim 1, wherein a compound of formula II or III is suspended in a solvent and then treated with HBr and a sulphoxide.

8. The process in accordance with claim 7, wherein a compound of formula II or III is suspended in ethyl acetate or acetic acid, followed by adding hydrogen bromide in acetic acid and then adding dimethylsulfoxide.

9. A process for preparation of amino substituted benzothiazole derivatives of formula I

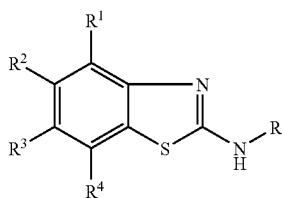

wherein
R¹, R² and R³ are independently from each other hydrogen, lower alkyl, lower alkoxy or halogen;
R⁴ is hydrogen, lower alkyl, lower alkyloxy, halogen, or is a five or six membered non aromatic heterocyclyl group, unsubstituted or substituted by lower alkyl or an oxo-group, or is
—NR⁵R⁶, wherein R⁵ and R⁵ are independently from each other hydrogen, lower alkyl, —C(O)-lower alkyl, —(CH₂)ₙO-lower alkyl or benzyl, optionally substituted by lower alkyl, or is a five or six membered heteroaryl group;
R¹ and R² or R² and R³ may form together with the corresponding carbon atoms a ring containing —O—CH₂—O— or —CH=CH—CH=CH—;
R is hydrogen or —C(O)R';
R' is a five or six membered non aromatic heterocyclyl group, five or six membered heteroaryl group or is aryl, which rings may be substituted by the groups, selected from lower alkyl, halogen-lower alkyl, lower alkoxy, cyano, nitro, —C(O)H, —C(O)OH or by pyrrolidin-1-yl-methyl;
n is 1 to 4;
or a pharmaceutically acceptable salt thereof, comprising dissolving a compound of formula

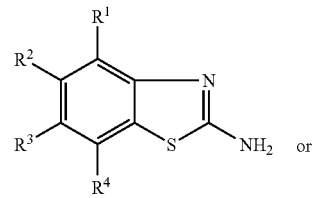

or

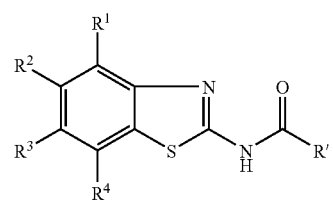

in ethyl acetate, adding hydrogen bromide in acetic acid, and then adding dimethylsulfoxide in one portion.

* * * * *